United States Patent [19]

Sguazzi

[11] 4,280,499

[45] Jul. 28, 1981

[54] ORYOTHERAPY APPARATUS

[75] Inventor: Angelo Sguazzi, Turin, Italy

[73] Assignee: Dario Bracco, Turin, Italy

[21] Appl. No.: 46,292

[22] Filed: Jun. 7, 1979

[30] Foreign Application Priority Data

Jun. 23, 1978 [IT] Italy ................. 68479 A/78

[51] Int. Cl.³ .................................. A61B 17/38
[52] U.S. Cl. ........................ 128/303.1; 62/52; 62/514 R
[58] Field of Search ............ 128/303.1, DIG. 27, 128/399, 400; 62/52, 53, 514 R, 293

[56] References Cited

U.S. PATENT DOCUMENTS

| | | | |
|---|---|---|---|
| 1,476,699 | 12/1923 | Fabret | 128/400 |
| 3,393,679 | 7/1968 | Crump et al. | 128/303.1 |
| 3,439,680 | 4/1969 | Thomas | 128/303.1 |
| 3,507,283 | 4/1970 | Thomas | 128/303.1 |

OTHER PUBLICATIONS

De Boo et al., Integrated Circuits & Semiconductor Devices pp. 117 and FIG. 7-21 (1977). TK 7871.85 D43.

*Primary Examiner*—Robert W. Michell
*Assistant Examiner*—Michael H. Thaler
*Attorney, Agent, or Firm*—Sughrue, Rothwell, Mion, Zinn and Macpeak

[57] ABSTRACT

Cryotherapy apparatus for effecting localised cooling of body tissue comprises an intensively cooled hollow probe extending from a handle. Cooling of the probe is effected by refrigerant passed through a capillary tube in the probe to expand and evaporate in a chamber near the probe tip. Passages in the probe and handle serve to supply and exhaust refrigerant from the capillary tube and chamber respectively. In order to prevent excessive cooling of the handle, automatic means are provided which upon the handle temperature falling below a threshold value are arranged to energise a pressure reducing valve to restrict refrigerant flow to the probe and simultaneously energise heating elements provided at the entry of the valve and in the handle.

1 Claim, 5 Drawing Figures

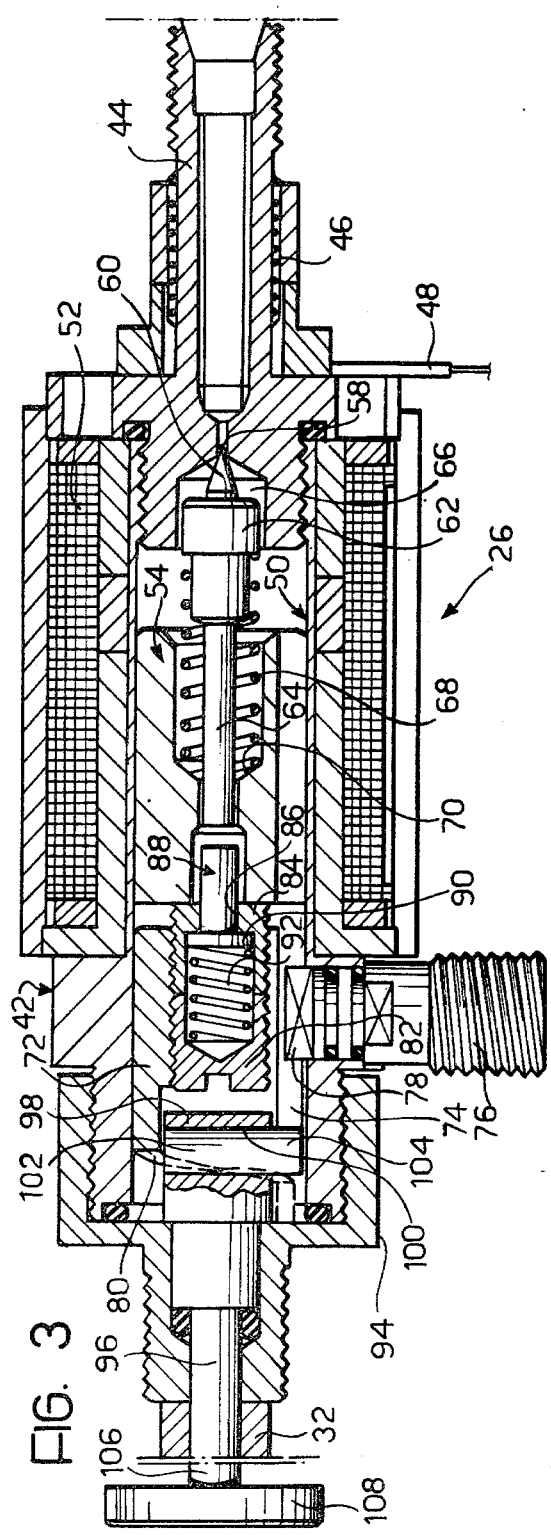
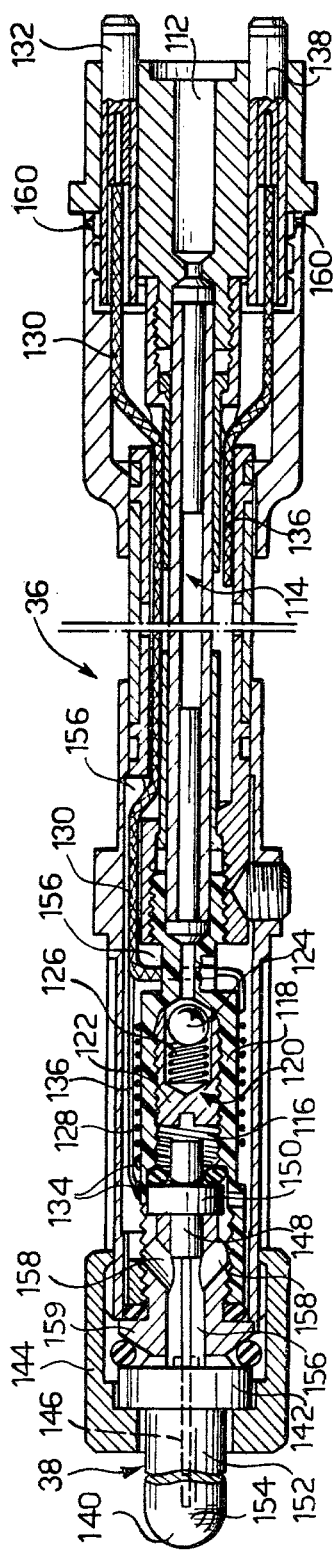
FIG. 3
FIG. 4

CRYOTHERAPY APPARATUS

DESCRIPTION

The present invention relates to cryotherapy apparatus of the kind comprising a tubular handle provided with an axial pipe defining therewith an annular passage, a refrigerant supply pipe connected to said axial pipe, and a tubular probe extending from the handle and closed at its end remote from the handle, the said probe containing an axial capillary tube communicating at one end with the axial pipe of the handle and terminating, at its opposite end, close to the closed end of the probe, the said capillary tube and tubular probe together defining a chamber surrounding the free end of the capillary tube and an annular passage communicating the chamber with the annular passage of the handle.

In operation of the apparatus, a pressurised, liquified refrigerant which has an evaporation temperature less than the ambient temperature, is fed via the supply pipe to the axial pipe of the handle from where it passes into the capillary tube to effect cooling of the probe by expansion and evaporation as it enters into the surrounding chamber of the probe. The expanded refrigerant is discharged through the annular passages in the probe and handle.

It is known that some kinds of cells of the human and animal body can be treated, and operated upon, in a more efficient manner by using refrigerating apparatus of the aforesaid kind to induce localised congealing of the body tissue at very low temperatures.

Such apparatus has for some time been used for therapeutic or surgical purposes, especially in such fields as otorhinolaryngology, urology, dermatology, neurosurgery, gynaecology, and ophthalmology.

In such cryotherapy apparatus, the problem arises that it is not possible in practice to provide an efficient thermal insulation between the probe and the handle which is held by the doctor or the surgeon during the operation. It has therefore been necessary to provide devices for adjusting the flow of the regrigerant in order to prevent excessive cooling of the handle.

In known cryotherapy apparatus, such devices generally consist of valves which are partly manually controlled so as to prevent the excess cooling produced by evaporation of the refrigerant within the probe, and not absorbed by the tissues, from causing freezing of the handle.

In these known devices, proper adjustment of the flow of refrigerant is wholly dependent on the sensitivity and dexterity of the operator, who is obliged, at the risk of dangerous consequences, to transfer his attention from the purely medical aspect of the operation to the technical aspect associated with this adjustment.

It is therefore an object of the present invention to effect automatic control of the apparatus such as to prevent excessive cooling of the handle while keeping the probe at a temperature appropriate for the therapeutic or surgical use intended.

In accordance with the present invention, temperature regulation in cryotherapy apparatus of the kind referred to, is effected by the provision of an electromagnetically operable pressure reducing valve connected into the refrigerant supply pipe and including a movable valve closure member arranged to give unrestricted or restricted flow of refrigerant through the valve in dependence on the state of energisation of an electromagnetic winding of the valve, a temperature sensor arranged to sense the temperature of the handle and to output a signal indicative of that temperature, a first electrical heating element arranged, when energised, to warm refrigerant entering the pressure reducing valve, a second electrical heating element located within the handle, and an electronic control circuit responsive to the temperature sensor output signal indicating that the handle temperature has fallen below a predetermined threshold value, to energise the first and second heating elements and to change the state of energisation of the electromagnetic winding of the valve to that in which flow through the pressure reducing valve is restricted.

In this manner, not only is the handle of the cryotherapy apparatus maintained at an appropriate temperature, but the amount of refrigerant supplied to the probe is also regulated to that actually required for an efficient cooling of body tissue thereby avoiding both the waste of refrigerant due to over-supply, and inadequate cooling of the probe due to undersupply.

Cryotherapy apparatus embodying the invention will now be particularly described, by way of example, with reference to the accompanying drawings, in which:

FIG. 3 is a view, partially in axial section, of a pressure reducing valve of the apparatus;

FIG. 4 is a view in axial section of a handle and probe of the apparatus; and

Figure 1:
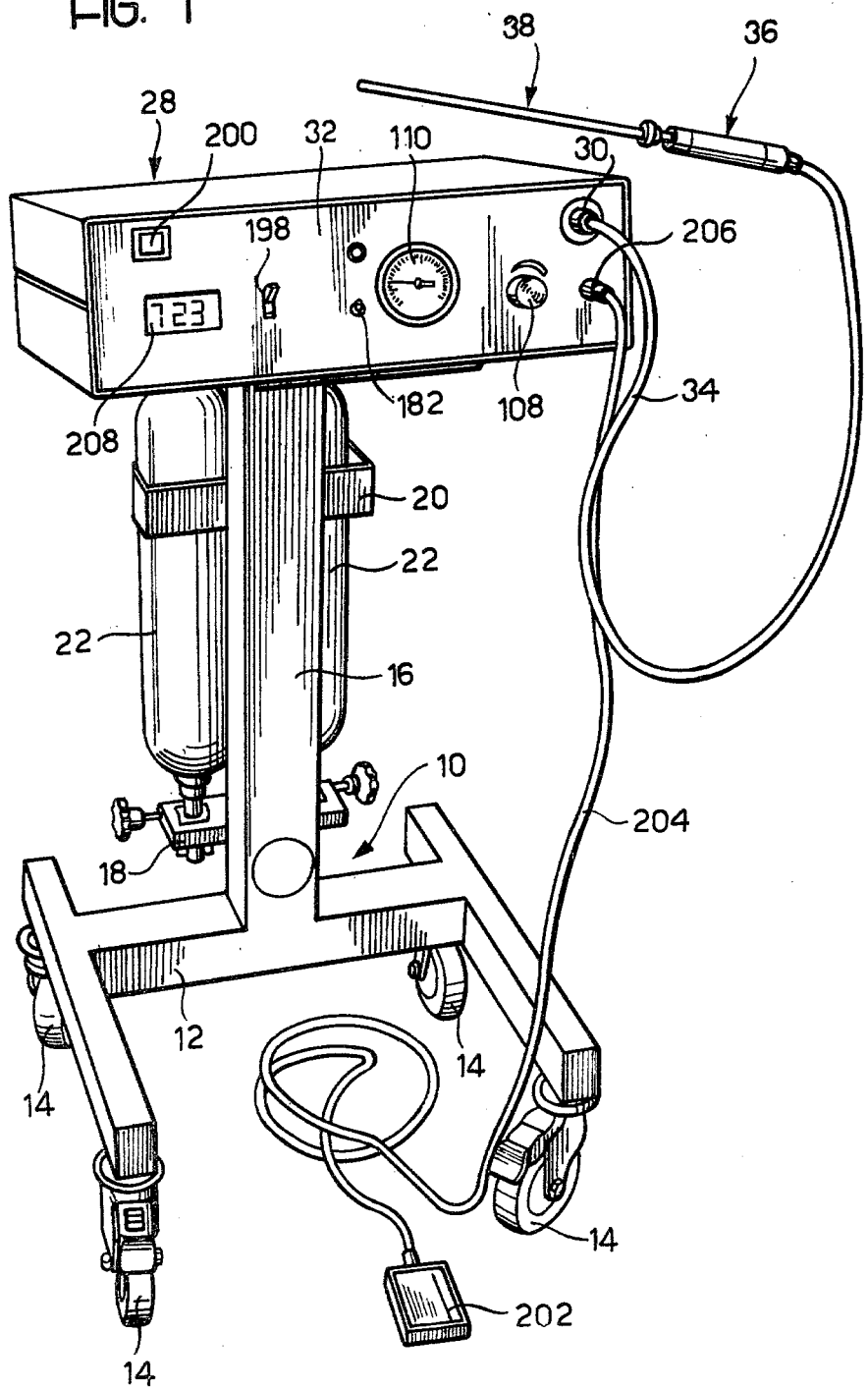
FIG. 1 is a perspective view of the cryotherapy apparatus.

As shown in FIG. 1, the cryotherapy apparatus includes a metal support structure 10 consisting of a column support 16 secured to the centre of an H-shaped lower frame 12, whose arms pivotally mount four wheels which give mobility to the apparatus.

The support 16 carries a transverse shelf 18 which together with a metal locking ring 20 serves to support a pair of pressurised containers 22. The containers 22 contain a liquified refrigerant which has an evaporation temperature less than the ambient temperature and which, for example, is anhydrous nitrogen oxide under a pressure of between 40 and 70 atmospheres.

Figure 2:
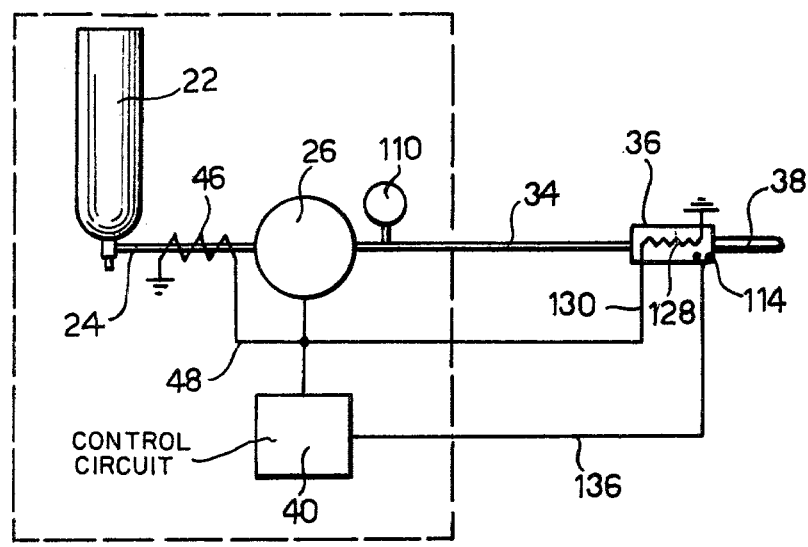
FIG. 2 is a diagrammatic representation of the apparatus.

As shown in FIG. 2, the containers 22 are connected via feed piping 24 to a pressure reducing valve 26 housed within a control box 28 (FIG. 1) mounted on the upper end of the support 16.

The pressure reducing valve 26 is connected, via a union 30 provided on a front control panel 32 of the control box 28 and a flexible pipe 34 connected to the union 30, to one end of a handle 36 which carries a probe 38 at its other end.

The pressure reducing valve 26 is of the electromagnetic kind, and is connected to an electronic control circuit 40, housed within the control box 28. The control circuit 40 will be described in more detail hereinafter.

The procedure reducing valve 26 is shown in FIG. 3, and comprises a tubular body 42 which terminates at one end in an inlet union 44 connected to the feed piping 24 and around the outer surface of which is wound an electrical resistance element 46. The element 46 is connected between electrical earth and an output of the electronic control unit 40.

An electromagnet 50 is housed within the tubular body 42 of the valve 26, close to the union 44. The electromagnet 50 consists of an electrical excitation winding 52, connected to the electronic control circuit 40, and a hollow magnetic core 54 axially slidable within the winding 52.

A rod 64 is arranged for axial sliding movement within the cavity of the magnetic core 54. At its end adjacent the union 44, the rod 64 has an enlarged cylindrical portion 62 to which is fixed a conical valve closure member 60. The cylindrical end portion 62 is arranged to slide in a cavity 66 of the union 44. The cavity 66 communicates via a narrow duct 58 formed in the union 44, with the interior of the piping 24. The conical valve closure member 60 carried by the rod 64 is axially urged by a helical spring 68 towards the inner end of the duct 58 which is formed as a valve seat. The helical spring 68 reacts between the cylinrdical end portion 62 of the rod and an internal shoulder 70 of the core 54.

A sleeve 72 is mounted for axial sliding movement within the tubular body 42 downstream of the magnetic core 54 (considered in terms of the direction of refrigerant flow through the body 42 from the piping 24 to the flexible pipe 34).

The sleeve 72 is held against rotation by means of a spline 78 which engages in a groove provided in the sleeve 72. The end face 80 of the sleeve 72, which is remote from the magnetic core 54, is helically contoured.

A union 76 extending transversely from the tubular body 42 serves for the outlet of the refrigerant. The union 76 communicates with the space around the valve closure member 60 via the groove 74 in the sleeve 72 and a groove in the magnetic core 54.

A hollow cylindrical element 82 is located within the sleeve 72 and coupled thereto by a threaded coupling. The end 84 of the element 82 facing the electromagnet 50 projects outside the sleeve 72 and bears against the opposed end face of the magnetic core 54.

The end 84 of the cylindrical element 82 has an axial hole which opens into the internal cavity of the element 82 and which slidably mounts a cylindrical rod 88. One end of the rod 88 extends within the cavity of the cylindrical element 82 and is formed with an enlargement 90 which is urged against the internal face of the end 84 by a helical spring 92 housed inside the cavity of the cylindrical element 82. The opposite end of the rod 88 extends into the cavity of the magnetic core 54, coaxial with the rod 64 which carries the valve closure member 60.

A nut 94 screw threadedly engages the end of the tubular body 42 opposite to the inlet union 44. A rotatable shaft 96 extends axially through the nut 94 in a sealing engagement therewith. The inner end 98 of the shaft 96 is housed coaxially within the sleeve 72. The shaft 96 has, close to this end 98, a radial hole 100 into which a pin 102 is shrink-fitted. One end 104 of the pin 102 projects beyond the surface of the shaft 96 and bears against the helically contoured front end face 80 of the sleeve 72.

That end of the shaft 96 which extends outside the tubular body 42 passes through the control panel 32 of the control box 28, and carries a control knob 108.

The outlet union 76 of the pressure reducing valve is connected via a pressure gauge 110 (FIG. 2), the indicator of which is located on the control panel 32, to the union 30, which in turn is connected via the flexible pipe 34 with the end 112 (FIG. 4) of an axial pipe 114 of the handle 36.

The pipe 114 has a constant cross-sectional area and extends through the handle 36 to the entry duct of a chamber 116 formed within a cylindrical element 118 made of insulating material.

A non-return valve 120 engages within the chamber 116 by means of a threaded coupling. The valve 120 consists of a cup element 122 sealing a ball 124 which is urged under the action of a helical spring 126, against the mouth of the entry duct extending from the pipe 114 to the chamber 116. The cup element 122 is so formed that refrigerant entering the chamber 116 can flow past the element 122.

A second electrical resistance element 128 is wound around the exterior of the cylindrical element 118. One end of the resistance element 128 is connected, via a lead 130 housed within the handle 36, to an electrical connecting pin 132 for conection to the electronic control circuit 40. The other end of the resistance element 128 is connected to the earth of the handle 36.

A thermocouple 134 is housed within the handle 36 close to the cylindrical element 118 and is connected, via two leads 136, which lead to two connecting pins 138 which serve to provide electrical connection to the electronic control circuit 40. The connecting pins 132 and 138 and concentrically arranged with respect to the end 112 of the pipe 114.

The tubular probe 38 has one closed end 140 and is provided at its opposite end with a connecting flange 142. The probe 38 is secured to the handle 36 by means of a nut 144, which threadedly engages the handle 36 and screws down onto the flange 142.

A capillary tube 146 which has a diameter in the order of 0.5 mm, extends coaxially into the probe 38. One end of the capillary tube 146 is sealingly fixed into a sleeve 148 which is located by means of a collar 150 within the cylindrical element 118 downstream of the valve 120. The sleeve 148 communicates with the chamber 116.

The free end of the capillary tube 146 remote from the sleeve 148 terminates close to the closed end 140 of the probe 38 to form with the said probe 38 an annular passage 152 opening into a chamber 154 delimited by the closed end 140 of the probe 38 and surrounding the free end of the capillary tube 146.

The chamber 154 and the annular passage 152 communicate, via a passageway 156 and three ducts 158 defined by a member 159 screwed into the end of the cylindrical element 118, with an annular passage 156 defined between the axial pipe 114 and the outer wall of the handle 36 and communicating with the atmosphere through apertures 160.

Figure 5:
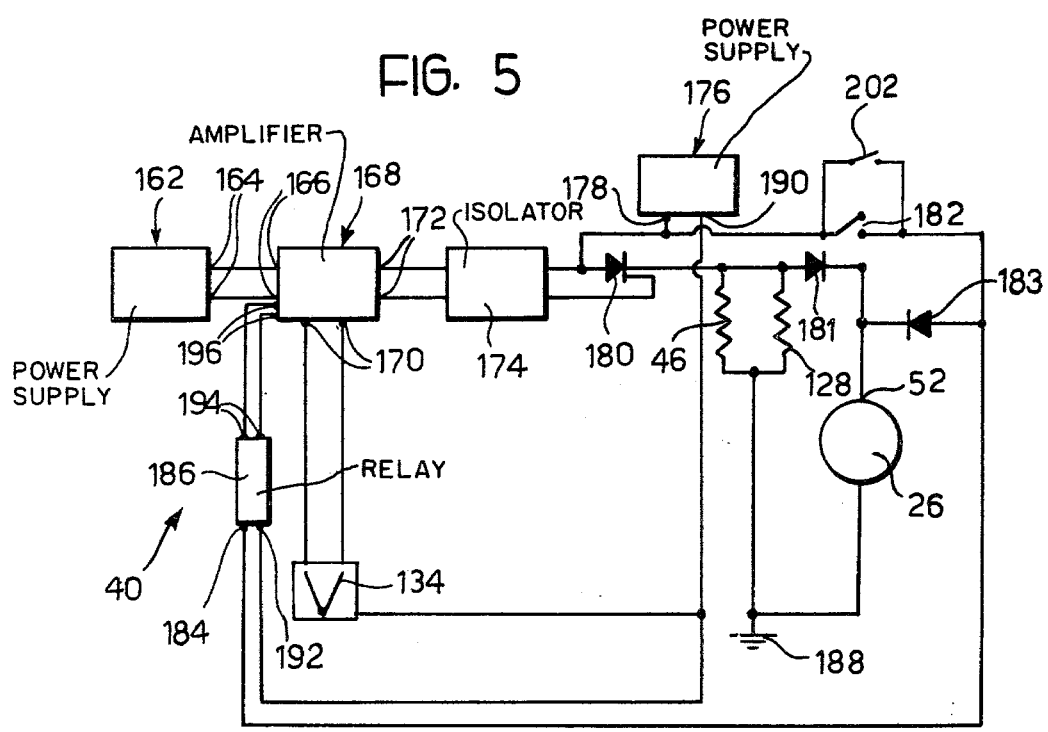
FIG. 5 is a block diagram of an electronic control circuit of the apparatus.

Referring now to FIG. 5, the electronic control circuit 40 housed within the control box 28 comprises a first stabilised power supply 162 which has an output 164 connected to a first input 166 of an amplifier 168. The amplifier 168 has a second input 170, connected to the thermocouple 134, and an output 172 connected, via an optical isolator 174, to an electronically controlled switching device in the form of a controlled diode 180. The controlled diode 180 is connected to a first output 178 of a second power supply 176 and upon triggering into conduction of the diode 180, the first output 178 is arranged to energise the heating elements 46 and 128 and, via a diode 181, the excitation winding 52 of the pressure reducing valve 26. The first output 178 of the second power supply 178 is also connected via a switch 182 mounted on the control panel 32 with the first input 184 of a relay 186. A diode 183 is arranged between the diode 181 and the switches 182, 202 in order to prevent the relay 186 from being energised when the controlled diode 180 is triggered into conduction and the switches 182, 202 are open. The electrical resistance elements 46 and 128 and the excitation winding 52 are also connected to earth 188.

The second power supply 176 has a second output 190 connected to a second input 192 of the relay 186 and to the thermocouple 134. The output 194 of the relay 186 is connected to a third input 196 of the amplifier 168.

By means of the electrical switch 182 mounted on the control panel 32 and connected to a warning light 200 (FIG. 1), or else by means of a pedal control 202 connected, by a lead 204, to a connection plug 206 mounted on the control panel 32, it is possible to change the threshold temperature as will be described below.

The control panel 32 of the control box 28 also carries a digital clock display 208 to give the operator an indication of the duration of the cryotherapy being performed.

The digital clock display 208 can be started, stopped or reset by means of a switch 198 mounted on the control panel 32.

Operation of the cryotherapy apparatus will now be described.

To initiate the supply of refrigerant under pressure into the axial pipe 114 of the handle 36, the operator turns the control knob 108 of the pressure reducing valve 26 to allow the sleeve 72 to move away from the inlet union end of the body 42 and thereby relieve the spring urging of the valve closure member 60 carried by the rod 64 towards the duct 58 in the inlet union 44. As the refrigerant enters the chamber 116 of the handle 36, its pressure is partially reduced owing to the action of the valve 120. This pressure reduction, whilst causing a negligible dissipation of thermal energy owing to the proximity of the probe 38, makes it possible to utilise a capillary tube 146 having a relativey large diameter (of the order, as stated, of 0.5 mm) without however, having to use excessive amounts of refrigerant to provide sufficient cooling. This, apart from facilitating the production of the said capillary tube 146, reduces the danger of obstructions being caused by impurities contained within the refrigerant.

The refrigerant passes, through the chamber 116 and the sleeve 148, into the capillary tube 146 and expands into the chamber 154. Since the cross-section of the chamber 154 is much greater than the cross-section of the capillary 146 a sudden expansion of the refrigerant occurs, which causes the refrigerant to evaporate and bring about a considerable lowering of temperature of the probe 38. By using the anhydrous oxide of nitrogen as the refrigerant, it is possible to obtain probe temperatures of around −89° C.

Following evaporation, the refrigerant flows out of the chamber 154 through the annular passage 152, the passageway 156, the pipes 158, and the annular passage 156 to finally discharge into the atmosphere through the apertures 160. The cooling caused by expansion and evaporation of the refrigerant is not limited in its effect solely to a heat exchange process with the probe 38, and cooling of the handle 36 and of the thermocouple 134 occurs during the outflow of the refrigerant through the annular pasage 156.

When the temperature signal supplied by the thermocouple 134 indicates that the handle temperature has fallen below a predetermined threshold value, the amplifier 168 is arranged to produce a control signal which, via the optical isolator 174, triggers the controlled diode 180 into conduction to cause energisation of the winding 52 and the electrical heating resistance elements 46 and 128 from the first output 178 of the supply 176.

The optical isolator 174 comprises a photo-diode and a cooperating phototransistor, and serves to electrically isolate the amplifier 168 from the earth connections of the resistance elements 46 and 128 and of the winding 52. This leads to a considerable simplification in construction without giving rise to harmful feedback to the input 170 of the amplifier 168.

As a result of energisation of the winding 52 of the pressure reducing valve 26, the core 54 is axially moved which in turn causes axial movement of the valve member 60 to partially close the narrow duct 58 which was previously fully open. Thus a reduction of pressure occurs in the refrigerant fed to the handle 36 which results in reduced cooling of the probe 38 and therefore of the handle 36.

At the same time, energisation of the resistance element 46 warms the inlet union 44 to compensate for lowering of the temperatue of the refrigerant owing to the pressure reduction caused by partial closure of the valve 26. The warming effect of the element 46 also induces evaporation of the refrigerant which makes the restricting action of the valve 26 more effective.

The warming effect of the electrical resistance element 128 aids the restoration of the temperature of the handle 36 to its correct value. Upon this temperature value being reached, the second supply 176 is deactivated by the thermocouple 134, and the resistance elements 46 and 128 and the winding 52 are de-energised. The magnetic core 54 returns to its position corresponding to complete opening of the duct 58.

By manual adjustment of the control knob 108 it is possible to vary the position of the valve closure member 60 in a continuous manner between a completely open and a completely closed position of the pressure reducing valve 26. As already outlined, manual operation of the valve 26 is effected by rotation of the knob 108 to cause the shaft 96 to rotate and move the end 104 of the pin 102 over the helically contoured end face 80 of the sleeve 72. This allows the sleeve 72 to move axially and, owing to the abutment of the end 84 of the cylindrical element 82 carried by the sleeve 72 and the corresponding end of the magnetic core 54, the force exerted upon the valve closure member 60 by the spring 68 can be adjusted. In its position corresponding to complete closure of the valve 26, the free end of the cylindrical rod 88 is urged against the end of the rod 64 by the helical spring 92. The spring action of the pin 88 makes it possible to prevent damage to the entry of the inled duct 58 by the closure member 60 when completely closing the duct 58.

The described manual adjustment arrangement of the valve 26 makes it possible to use the cryotherapy apparatus for carrying out cryotherapy operations without danger of freezing up of the handle 36 even if the electronic control circuit 40 should break down or the electricity supply fail.

After use of the apparatus, it is possible to return the probe very quickly to ambient temperature by operating the switch 182 or the pedal controlled swith 202.

Upon closure of the switch 182 or of the switch 202, the relay 186 is excited which causes the threshold temperature below which the amplifier 168 produces an output to be raised relative to that applicable during use of the apparatus. The excitation winding 52 and the electrical heating resistance elements 46 and 128 are consequently energised from the second power supply 176 until the heating effects of the resistance elements 46 and 128 restores the temperature of the probe to a value near to ambient temperature.

I claim:

1. Cryotherapy apparatus comprising:

a tubular handle having an axial pipe defining therewith an annular passage, a tubular probe extending from the handle and closed at its end remote therefrom, the said probe containing an axial capillary tube communicating at one end with the said axial pipe of the handle and terminating at its opposite end close to the closed end of the probe, the said capillary tube and tubular probe together defining a chamber surrounding the free end of the capillary tube and an annular passage communicating the chamber with the annular passage of the handle, a supply pipe for supplying pressurised refrigerant having an evporation temperature less than the ambient temperature to said axial pipe of the handle in order to effect cooling of the probe by expansion and evaporation of the refrigerant as it passes from said capillary tube into said surrounding chamber of the probe, the expanded refrigerant being discharged through said annular passages, an electromagnetically-operable pressure reducing valve connected into the refrigerant supply pipe and including a movable valve closure member arranged to give unrestricted or restricted flow of refrigerant through the valve in dependence on the state of energisation of an electromangetic winding of the valve, a temperature sensor arranged to sense the temperature of the handle and to output a signal indicative of that temperature, a first electrical heating element arranged, when energized to warm refrigerant entering the pressure reducing valve, a second electrical heating element located within the handle, and an electronic control circuit responsive to the temperature sensor output signal indicating that the handle temperature has fallen below a predetermined threshold value, to energise the first and second heating elements and to change the state of energisation of the electromagnetic winding of the valve to that in which flow through the pressure reducing valve is restricted;

said pressure reducing valve comprising:

a tubular body provided with an inlet union for connection to the refrigerant supply pipe, an electromagnet housed in the tubular body adjacent the inlet union and comprising said winding controlled by the electronic control circuit and a hollow magnetic core axially slidable within the winding, a rod movable in response to movement of the magnetic core and carrying at one end the valve closure member, said closure member being arranged to cooperate with a valve seat provided in the inlet union, an outlet union for refrigerant provided on the side of the tubular body downstream of the electromagnet, and manually operable control means arranged to vary the position of the valve closure member with respect to said valve seat in a continuous manner between positions corresponding to complete opening and complete closure of the pressure reducing valve;

said manually operable control means comprising:

a sleeve axially slidable but non-rotatably mounted within the tubular body downstream of the electromagnet, the said sleeve being provided with a peripheral axial groove communicating with the said outlet union and the end face of the said sleeve remote from the electromagnet being helically contoured, a hollow, cylindrical element threadedly engaging within the sleeve, the end of the said cylindrical element facing towards the electromagnetic projecting outside the sleeve so that it can abut against the magnetic core of the said electromagnet, a rod member slidably mounted in an axial opening made in the said end of the hollow cylindrical element facing the electromagnet, one end of the rod member extending into the interior of the magnetic core coaxially with the rod mounting the valve closure member and the opposite end of the rod member being provided with an enlargement located within the internal cavity of the said hollow cylindrical element, resilient means for urging said enlargement of said rod against the said end of the hollow cylindrical element provided with the axial opening mounting the rod member, a rotatably mounted shaft extending through the end of the tubular body opposite to the inlet union, the end of the shaft outside the tubular body being provided with a control knob, and a pin located in a radial hole made in the shaft adjacent its inner end, the said pin having one end projecting from the radial hole to engage the helically contoured end of the sleeve so that the rotation of the shaft by means of the control knob is effective to cause axial movement of the sleeve and of the magnetic core resulting in movement of the valve closure member between completely open and completely closed positions, the said one end of the rod member being arranged to abut against the rod carrying the closure member when the latter is in said completely closed position.

* * * * *